(12) United States Patent
Braun

(10) Patent No.: US 7,241,289 B2
(45) Date of Patent: Jul. 10, 2007

(54) SURGICAL INSTRUMENT

(76) Inventor: Marcus Braun, Heerstrasse 25, 70563, Stuttgart-Vaihingen (DE)

( * ) Notice: Subject to any disclaimer, the term of this patent is extended or adjusted under 35 U.S.C. 154(b) by 463 days.

(21) Appl. No.: 10/815,411

(22) Filed: Apr. 1, 2004

(65) Prior Publication Data

US 2004/0260336 A1 Dec. 23, 2004

(30) Foreign Application Priority Data

Apr. 1, 2003 (DE) ................. 103 14 827

(51) Int. Cl.
*A61B 17/00* (2006.01)
(52) U.S. Cl. .................... 606/1; 606/205; 606/208
(58) Field of Classification Search ............. 606/1, 606/51–52, 205–208
See application file for complete search history.

(56) References Cited

U.S. PATENT DOCUMENTS

| 5,174,300 | A | * | 12/1992 | Bales et al. ............... 600/564 |
| 5,275,608 | A | * | 1/1994 | Forman et al. ............ 606/170 |
| 5,330,502 | A | * | 7/1994 | Hassler et al. ............. 606/205 |
| 5,350,391 | A | * | 9/1994 | Iacovelli .................... 606/170 |
| 5,374,277 | A | * | 12/1994 | Hassler ..................... 606/207 |
| 5,472,451 | A | * | 12/1995 | Freitas et al. .............. 606/205 |
| 5,474,571 | A | * | 12/1995 | Lang ......................... 606/205 |
| 5,540,375 | A |   | 7/1996 | Bolanos et al. |
| 5,545,148 | A | * | 8/1996 | Wurster ..................... 604/223 |
| 5,549,637 | A | * | 8/1996 | Crainich ................... 606/207 |
| 5,582,617 | A | * | 12/1996 | Klieman et al. ........... 606/170 |
| 5,603,723 | A | * | 2/1997 | Aranyi et al. ............. 606/205 |
| 5,607,450 | A | * | 3/1997 | Zvenyatsky et al. ....... 606/206 |
| 5,609,601 | A | * | 3/1997 | Kolesa et al. .............. 606/170 |
| 5,643,294 | A | * | 7/1997 | Tovey et al. ............... 606/148 |
| 5,702,408 | A | * | 12/1997 | Wales et al. ............... 606/139 |
| 5,743,456 | A | * | 4/1998 | Jones et al. ............... 227/176.1 |
| 5,820,009 | A |   | 10/1998 | Melling et al. |
| 5,827,323 | A | * | 10/1998 | Klieman et al. ........... 606/205 |
| 5,997,565 | A | * | 12/1999 | Inoue ........................ 606/205 |
| 6,010,523 | A |   | 1/2000 | Sabin |
| 6,068,647 | A | * | 5/2000 | Witt et al. ................. 606/205 |
| 6,666,854 | B1 | * | 12/2003 | Lange ........................ 606/1 |
| 6,889,116 | B2 | * | 5/2005 | Jinno ........................ 700/245 |
| 6,936,061 | B2 | * | 8/2005 | Sasaki ...................... 606/205 |
| 2002/0040217 | A1 | * | 4/2002 | Jinno ........................ 606/1 |
| 2002/0055758 | A1 | * | 5/2002 | Sasaki ...................... 606/205 |

FOREIGN PATENT DOCUMENTS

DE 10036108 A1 11/2001

\* cited by examiner

*Primary Examiner*—Michael Peffley
*Assistant Examiner*—Alex B. Toy
(74) *Attorney, Agent, or Firm*—Mayer, Brown, Rowe + Maw, LLP

(57) ABSTRACT

A surgical instrument comprising an instrument handle which is linked to a proximal end portion of a tube shaft and at the distal end portion of which an instrument head rotatably supporting an effector is linked so as to be inclinable. The effector includes at least one pivotable engaging element which is operable via an effector operating gear train in cooperation with the instrument handle. The effector operating gear train, in turn, has a pushing rod which is shiftably supported in the tube shaft and which, in the linking area of the instrument head at the tube shaft, abuts a pushing pin shiftably supported in the instrument head, the pushing pin being operatively connected to the engaging element.

11 Claims, 5 Drawing Sheets

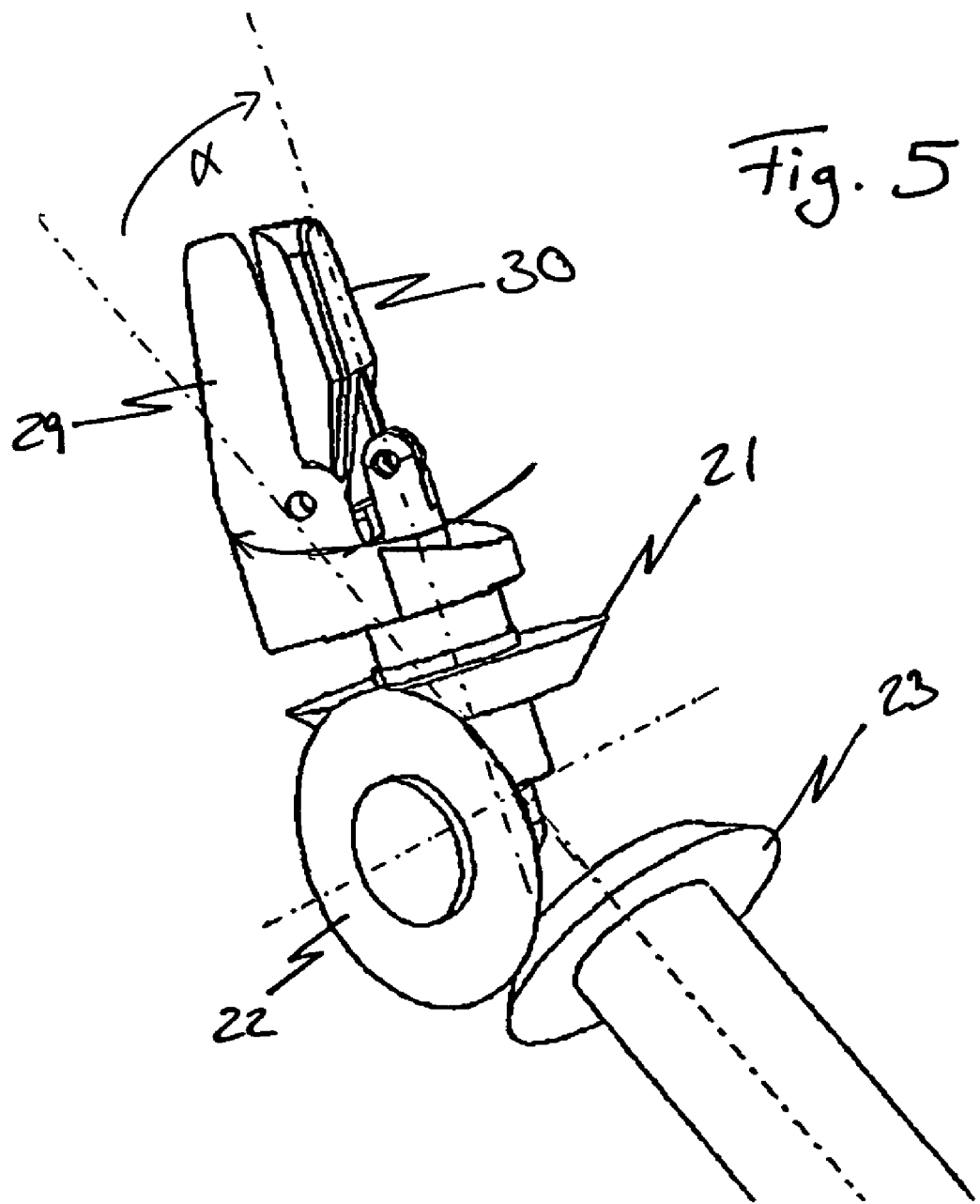

SURGICAL INSTRUMENT

BACKGROUND OF THE INVENTION

1. Field of the Invention

The present invention relates to surgical instrument for minimally invasive surgery.

2. Discussion of the Prior Art

From DE 100 36 108, a surgical instrument of this generic type is known. It substantially consists of a tube shaft at the one proximal end of which an instrument handle is arranged for the operation of an instrument head disposed at the opposed distal end of the tube shaft via gear trains. The instrument head can be pivoted and/or inclined with respect to the tube shaft and, moreover, holds an effector rotatably supported in the instrument head in the form of a type of forceps or tongs one jaw of which is pivotably supported on the effector and is likewise operable by means of the instrument handle.

In more concrete terms, the gear trains enable at least a first movement of the instrument handle, according to this prior art to be triggered by the rotation of an operator's hand, to be transformed into a rotation of the effector at a predetermined transmission ratio with respect to this operating movement. This makes it possible to rotate the effector despite the relatively restricted possibility of motion of a human hand about up to 300°, for instance, and, thus, to realize complex motions without changing the grip at the handle. Moreover, a second movement of the instrument handle, for instance bending the same with respect to the tube shaft, is converted into an inclination movement of the instrument head.

The gear trains provided inside the instrument handle and the tube shaft are designed such that a most largely decoupled operation of each individual movement of the instrument head and the effector is permitted. However, such gears are necessarily extremely complex and, consequently, also require sufficient assembly space. Moreover, a complete decoupling of the individual movements is not completely ensured.

In view of this prior art, it is the object of the present invention to provide a surgical instrument of this generic type in which motions of an instrument head as well as of an effector can be performed decoupled from each other via an instrument handle.

SUMMARY OF THE INVENTION

This object is achieved by a surgical instrument comprising an instrument handle linked at a proximal end portion of a tube shaft, the tube shaft having a distal end portion linked to an instrument head rotatably supporting an effector, the effector being inclinable relative to the tube shaft, wherein the effector further comprises at least one pivotable engaging element operable via an effector operating gear train in cooperation with the instrument handle. The effector operating gear train further comprises a pushing rod shiftably arranged in the tube shaft, and in a linking area between the instrument head and the tube shaft the pushing rod abuts a pushing pin. The pushing pin is shiftably supported in the instrument head and/or the effector and operatively connected to the engaging element.

Accordingly, the core of the invention consists in the fact that the effector operating gear train includes a pushing rod which is shiftably arranged in the tube shaft and which, in the linking area of the instrument head at the tube shaft, is in contact with a pushing pin shiftably supported in the instrument head or in the effector itself, the pushing pin being operatively connected to the engaging element. In this way, a pushing motion is transmitted to the pushing pin independently of the position of inclination of the instrument head with respect to the tube shaft without complex deflection gear mechanisms being required.

An especially advantageous configuration of the invention provides that the pushing rod has a distal front face which forms the engaging portion with the pushing pin and which is chamfered at a predetermined angle of preferably 45° in the bending direction of the instrument head. This measure provides a kind of power deflection means, whereby an advance motion of the pushing rod can be optimally transmitted to the pushing pin independently of the bending position of the instrument head.

Further advantageous configurations of the invention are the subject matter of the dependent claims.

BRIEF DESCRIPTION OF THE DRAWINGS

Hereinafter, the invention will be explained in detail by example of a preferred embodiment with reference to the accompanying drawings, in which:

FIG. 5 shows a partial section of the second gear train in the pivoting range of the instrument head.

DETAILED DESCRIPTION OF THE PREFERRED EMBODIMENTS

Figure 1:
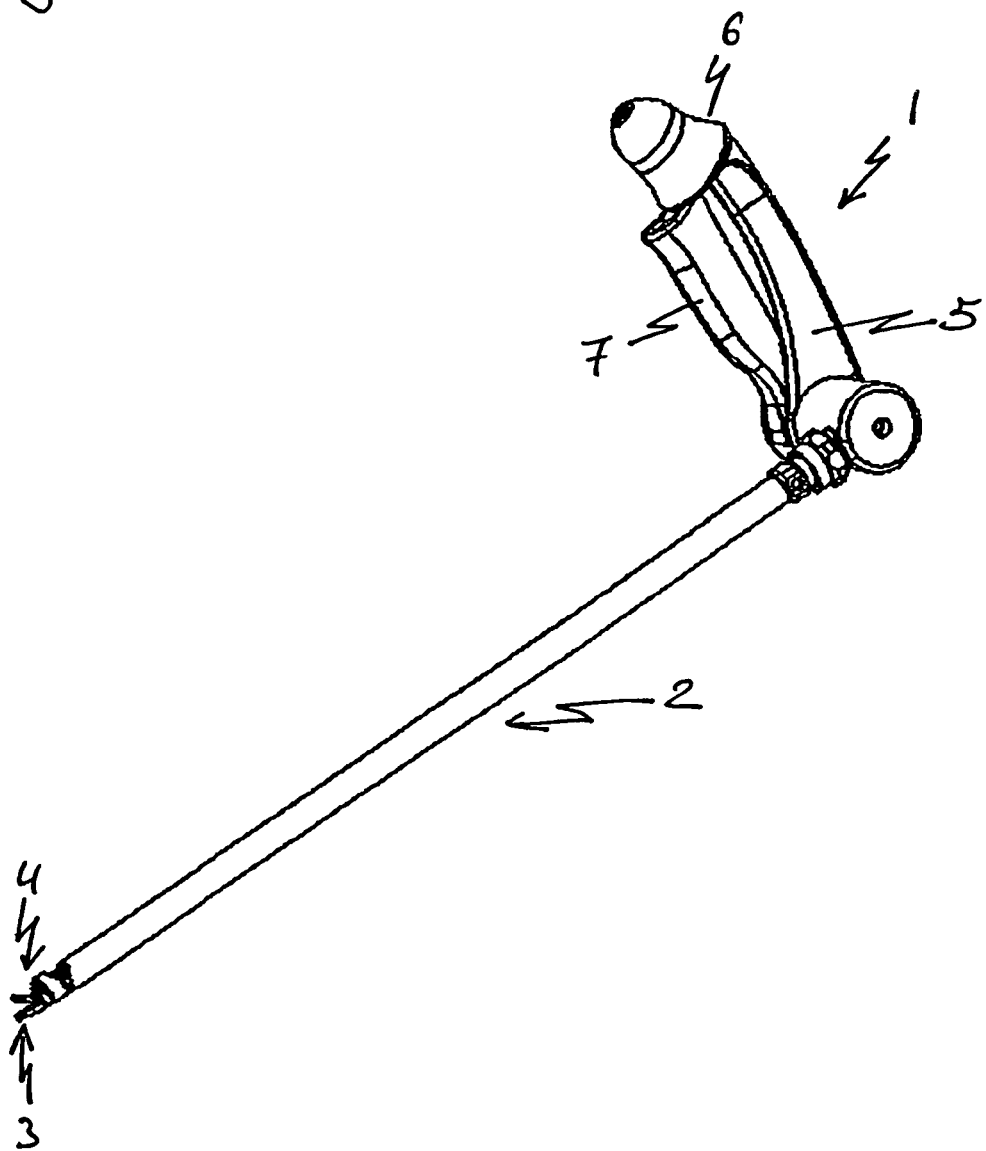
FIG. 1 shows a perspective view of a surgical instrument according to a preferred embodiment of the invention.

In FIG. 1, a complete surgical instrument according to a preferred embodiment of the invention is shown in a perspective view. The surgical instrument according to the invention consequently has a multi-functional instrument handle 1 which is arranged at a proximal end or end portion of a tube shaft 2, preferably made of stainless steel, a steel alloy or a synthetic material, as well as an instrument head 4 equipped or adapted to be equipped with an effector 3, the instrument head being provided at the other, distal end of the tube shaft 2.

In general, the instrument head 4 is supported at the respective tube shaft end such that it can be pivoted or bent with respect to the tube shaft 2, whereas the effector 3 can be turned or rotated in each bending position of the instrument head 4 about the longitudinal axis of the latter, the two aforementioned motions being adapted to be performed by means of the instrument handle 1. To this end, a number of manipulators or operating mechanisms are provided at the instrument handle 1 and are operatively connected, via corresponding gear trains inside the instrument handle 1 as well as inside the tube shaft 2, to the instrument head 4 and the effector 3, respectively, so as to be able to perform the individual motions of the instrument head 4 and of the effector 3 independently of each other, i.e. in a decoupled manner.

Specifically, the instrument handle 1 consists of an ergonomically shaped handle piece 5 which is mounted in a pivotable and inclinable manner to the tube shaft 2 and on which a first manipulator 6, in the present case preferably in the form of a rotary knob, and a second manipulator 7, in the present case preferably in the form of a handle lever, are supported. Thus, the instrument handle 1 according to the preferred embodiment of the present invention comprises a total of three operating mechanisms for three independent movements of the effector 3 and/or the instrument head 4, respectively. It is explicitly emphasized in this context that the instrument handle 1 may also have fewer operation possibilities, for instance only one manipulator or operating mechanism, respectively, for pivoting the instrument head 4 and rotating the effector 3.

Figure 2:
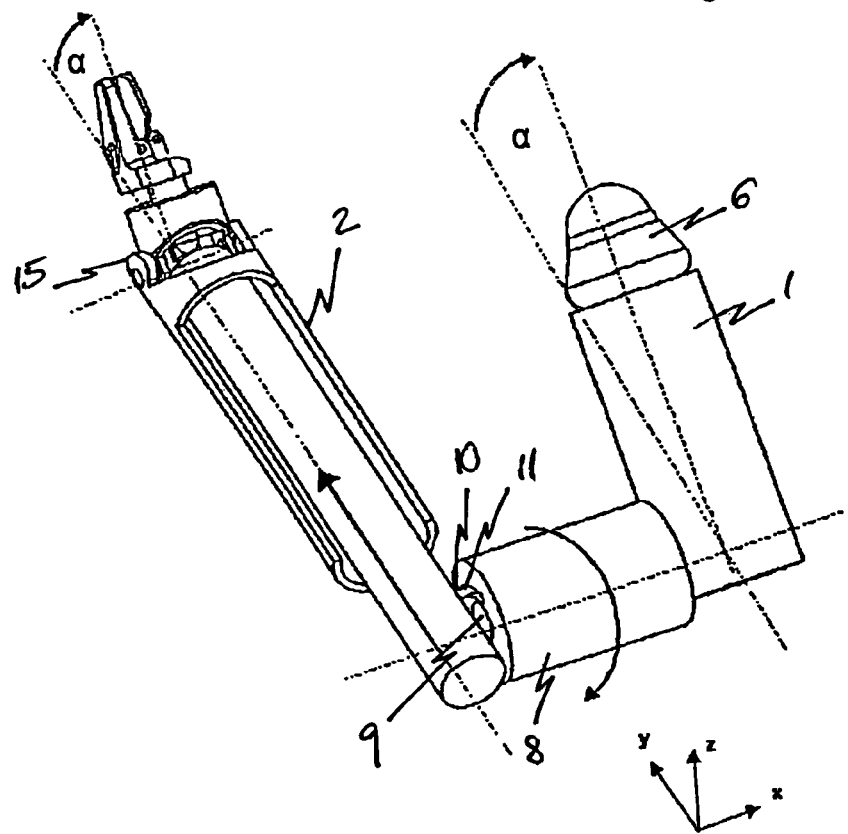
FIG. 2 shows a first gear train for pivoting an instrument head by means of an instrument handle.
Figure 3:
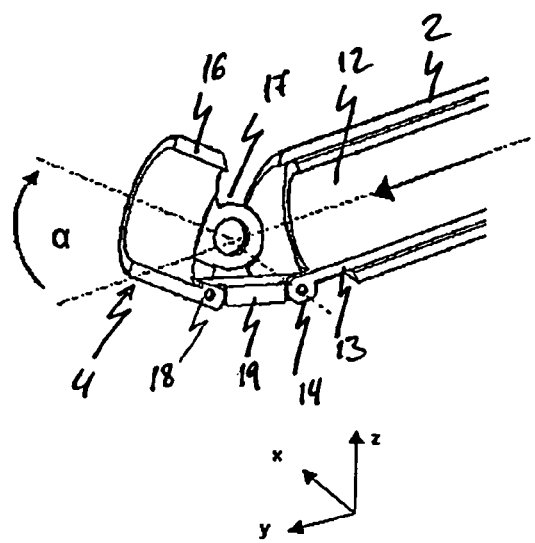
FIG. 3 shows a partial section of the first gear train in the pivoting range of the instrument head.

The exterior structure of the instrument handle 1, especially with respect to the operating mechanism for pivoting and bending the instrument head 4 and with respect to the corresponding bending gear train is shown in FIGS. 2 and 3.

The handle 1 schematically shown in FIG. 2 is pivotably connected to the tube shaft 2 via a crank member 8 which is fixedly connected to the handle member 5 and has the form of a rotary shaft or rotary disk. The rotary shaft 8 is preferably aligned so as to be perpendicular to the tube shaft 2 as well as to the handle member 5 and spaces the handle member 5 from the tube shaft 2 such that the handle 1 can be pivoted substantially in parallel to the tube shaft 2 past the same.

The rotary shaft 8, forming a central through passage 9 for accommodating the gear members described hereinafter, is shaped at its one front face facing the tube shaft 2 to have a crank guide 10 in the form of a cam-shaped groove in which a driving pin 11 engages which is attached to an axially shiftable pushing tube 12 supported in the tube shaft 2. The groove 10 is formed such that, during a rotation of the rotary shaft 8, the driving pin 11 slides along in the groove 10 by an appropriate pivoting of the handle member 5 and, in so doing, performs a forced compensating motion in the longitudinal direction of the tube shaft 2, said motion being transmitted to the pushing tube 12 and resulting in a reciprocating motion of the pushing tube 12 inside the tube shaft 2 depending on the direction of rotation of the rotary shaft 8.

The distal end portion of the pushing tube 12 opposite to the crank member 8 is formed so as to have a longitudinally extending mounting link 13 which projects from the distal end of the pushing tube 12 and forms a hinge or hinge eyes 14 at its free end portion. Moreover, the front face of the tube shaft 2 is chamfered at its distal end portion at an angle of preferably 45° and includes lateral link eyes 15 to which the instrument head 4 is pivotably linked via link joints or pins. The instrument head equally consists of a tube member 16 at whose one end control eyes 17 for connection to the tube shaft 2, or rather to the link eyes 15 thereof, are formed is likewise chamfered at an angle of preferably 45°, namely in such manner that, after linking the instrument head 4 to the tube shaft 2, the two aforementioned chamfers complement each other and enable the tube member 16 to be bent with respect to the tube shaft 2 by approximately 90°, preferably 70°.

Moreover, a hinge, or rather pivot eyes 18, are formed at the chamfered end of the tube member 16. To each of the pivot eyes 14; 18 provided at the pushing tube side and the tube member side, a rocking lever 19 is hinged, is consequently offset radially outwardly with respect to the pivot axis of the instrument head 4 and transmits an axial translation movement of the pushing tube 12 to the tube member 16 whereby the latter is pivoted about its own pivot axis.

Figure 4:
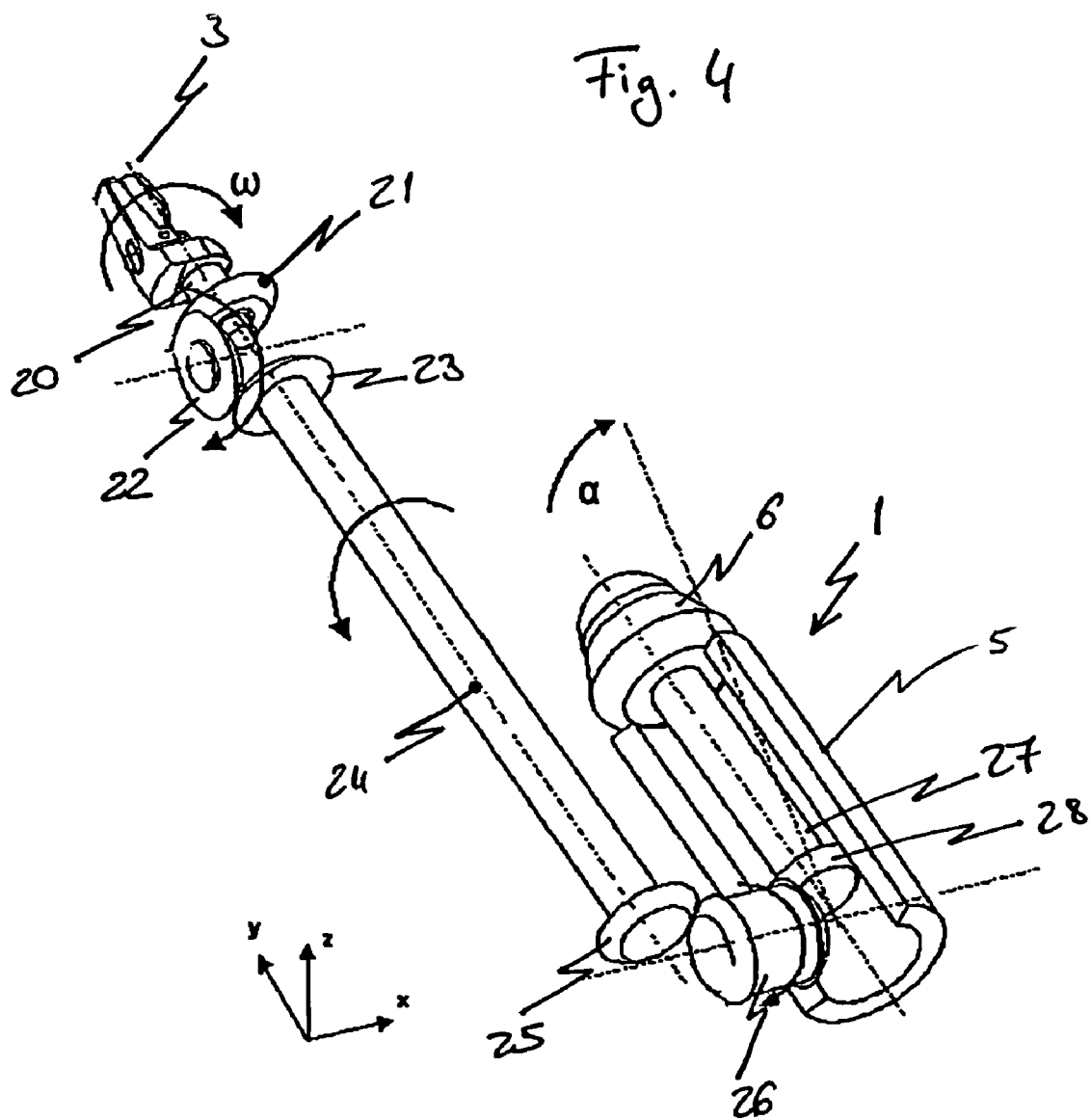
FIG. 4 shows a second gear train for rotation of the instrument head by means of the instrument handle.

Hereinafter, the operating mechanism for a rotation of the effector 3 supported in the instrument head 4 and the corresponding rotation gear train are described by way of FIG. 4 and FIG. 5.

As can be further be taken from FIG. 2, the aforementioned tube member 16 of the instrument head 4 at the same time constitutes a housing or receptacle for the effector 3. Independently of the type of effector, i.e. independently of whether, for instance, a needle holder, tongs, forceps or scissors are used as effector, the latter has a preferably hollow rotational shaft 20 which is rotatably inserted in the tube member 16 of the instrument head 4 and is secured against an axial movement. The length of this rotational shaft is selected such that it ends approximately in the area of the pivot axis of the instrument head 4 and is provided at its free end projecting toward this pivot axis with an output spur gear 21 which is attached to the rotational shaft 20 of the effector 3 in a torque-proof manner. Especially in FIG. 2, the pivot axis of the instrument head 4 is shown by a broken line through the eyes 15.

As can further be taken from FIG. 5, a torque transmission spur gear 22 is provided on the pivot axis of the instrument head 4, is rotatably supported on one of the two pivot pins of the instrument head 4, not shown in detail, which form the schematically shown pivot axis, and is in mesh with the output spur gear 21. The torque transmission spur gear 22, in its turn, is in mesh with a drive spur gear 23 which is mounted in a torque-proof manner on a drive shaft 24 rotatably guided inside the pushing tube 12 (not shown in FIGS. 4 and 5), as this is especially shown in FIG. 4. According to FIG. 4, another torque initiating spur gear 25 is arranged in a torque-proof manner on a drive shaft 24 rotatably guided inside the pushing tube 12 (not shown in FIGS. 4 and 5), as this is especially shown in FIG. 4. According to FIG. 4, at one end of the drive shaft 24 opposed to the drive spur gear 23, another torque initiating spur gear 25 is arranged in a torque-proof manner and is in mesh with a long-face pinion 26 supported in the central through passage 9 formed inside the crank member 8. The crank member 8 is not shown in detail in FIG. 4.

Finally, the long-face pinion 26 is in mesh with an actuating shaft 27, or rather a spur gear 28 fastened thereto, inside the handle 1, said shaft being fixedly connected to the one manipulator, the rotary knob 6 in the present case.

When the rotary knob 6 is operated, the rotation thereof is transmitted via the actuating shaft 27 inside the handle 1, the long-face pinion 26, the subsequent drive shaft 24 inside the pushing tube 12 as well as the transmission spur gear 22 to the effector 3, and the latter is turned. The rotary knob 6 is advantageously operated by the fingers, especially by the thumb and the index of the operator's hand, while the handle member 5 is held in the hand. Thus, it is possible to generate any rotation at the effector 3 without the operator having to change his grip at the handle member 5 itself. In this context, it is further referred to the fact that the drive shaft 24 and the pushing tube 12 are arranged in the axial direction so as to be relatively movable with respect to each other, i.e., a rotation of the crank member 8 triggered by pivoting the handle 1 does cause a translation movement of the pushing tube 12. Yet, at the same time, the drive shaft 24 is held in position, i.e. in mesh with the long-face pinion 26, whereby the pushing tube 12 performs an axial relative movement with respect to the tube shaft 2 and to the drive shaft 24.

Ultimately, hereinafter the operating mechanism for the effector 3, i.e. the functions thereof, and for the corresponding effector gear train is described by reference to FIGS. 5 and 6a–6c.

According to FIG. 5, in the present embodiment of the invention, the effector 3 is designed as tongs including a fixed jaw and a movable, i.e. pivotable jaw 29; 30. The fixed jaw 29 forms a unit together with the rotating shaft 20 of the effector 3 and is preferably formed integrally with the rotating shaft 20, whereas the movable jaw 30 is linked to the fixed jaw 29 at one end.

The movable jaw 30 forms a linking point 31 for a pushing pin 32 which is supported inside the rotating shaft 20 so as to be relatively shiftable, so that a pivoting movement of the movable jaw 30 with the maximum possible transmission is caused by the axial shifting of the pushing pin. As this is especially shown in FIGS. 6a–6c, the pushing pin 32 is biased by a spring 33 axially in the opening direction of the tongs enclosing the pushing pin 32 inside the rotating shaft 20. For this purpose, the pushing pin 32 has a shaft protrusion at which the biasing spring 33 is supported by its one end. The other end of the biasing spring 33 is supported against the fixed jaw 29. An end piece 34 of the pushing pin 32 projecting from the rotating shaft 20 towards the pivot axis of the instrument head 4 is formed as a ball-shaped head, the radius of the ball-shaped head 34 preferably being approximately 2.5 mm in the present case.

The aforementioned drive shaft 24 for rotating the effector 4 supported in the instrument head 4 is provided with a substantially continuous axial bore (not shown in detail). In this axial bore, a pushing rod 35 is guided to be axially shiftable as well as rotatably guided relative to the drive shaft 24, the front face of the pushing rod facing the pushing pin 32 being chamfered in accordance with the chamfers of the distal end provided at the tube shaft side and the pushing tube side, i.e. preferably 45° in the same direction. The pushing pin 32 is biased against this chamfered front face of the pushing rod 35 by the spring 33 and abuts against the same. The contact face between the pushing rod 35 and the pushing pin 32 is substantially punctiform due to the aforedescribed ball-shaped head of the pin 32, namely independently of the degree of bending of the instrument head 4 and independently of the position of rotation of the effector 3.

Figures 6A, 6B, 6C:
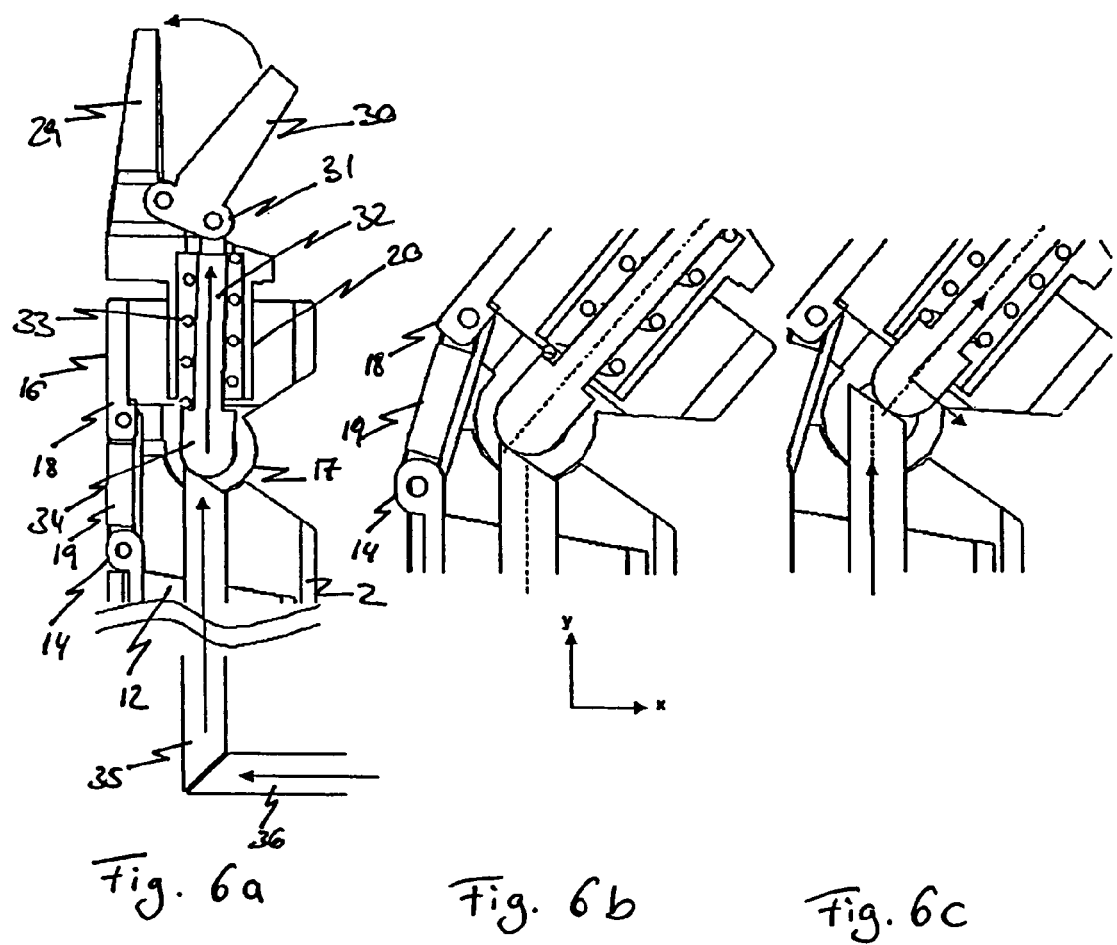
FIGS. 6a–6c show sectional views of a third gear train in the pivoting range of the instrument head for the operation of forceps supported at the instrument head.

As can be seen from FIG. 6a, the pushing pin 32 as well as the pushing rod 35 are aligned axially with respect to each other in case that the bending of the instrument head 4 with respect to the tube shaft 2 is substantially 0°. Moreover, in this position of the instrument head 4, the pushing pin 32 is positioned such that the center of the ball head 34 of the pushing pin 32 is located approximately in the pivot axis of the instrument head 4.

At its proximal end, the pushing rod 35 is connected, via a gear mechanism 36 not shown in detail, to the actuating lever 7 which is pivotably supported on the handle 1, as already briefly explained at the beginning of this description.

The functioning of the surgical instrument according to the invention will be described hereinafter in detail.

A rotation of the effector 3 supported in the instrument head 4 is effected by an operation of the rotary knob 6 supported at one end of the handle 1, the rotary knob 6 being adapted to be turned about its axis of rotation, as already described in the foregoing, so far that a rotation of approximately 360° is realized for the effector 3 without the necessity to change the grip at the handle member 5. This rotation is transmitted via the actuating shaft 27 to the long-face pinion 26 which, in its turn, transmits its rotation to the drive shaft 24 extending inside the pushing tube 12. The rotation of the drive shaft 24 causes a rotation of the transmission spur gear 22 which quasi bridges the pivot axis of the instrument head 4 and, thus, triggers a motion of rotation of the effector 3 inside the tube member 16 of the instrument head 4 about the axis of the tube member.

According to the present embodiment, the entire handle 1 has to be pivoted about the longitudinal axis of the crank member 8 to effect a bending, i.e. a pivoting movement of the instrument head 4 and, thus, of the effector 3. In other words, a pivoting movement of the handle 1 with respect to the tube shaft 2 causes a rotation of the crank member 8 connected to the handle 1 in a torque-proof manner. At the same time, however, the long-face pinion 26 is rotated along with the crank member 8 due to the fact that a kind of automatic lock by friction (efficiency of the gear mechanism) occurs by the mesh between the actuating shaft 27 and the long-face pinion 26, said lock being possibly further assisted by slightly holding the operating knob 6 and by the static friction between the operating knob 6 and the handle member 5.

The rotation of the crank member 8 is transmitted via the crank or rather groove 10 at the end of the member 8 as well as the driving pin 11 into an axial movement of the pushing tube 12, which is transformed via the hinged rocking lever 19 into a pivoting movement of the instrument head 4 about the pivot axis thereof. However, this pivoting movement is automatically also performed by the output spur gear 21 which is fixed to the rotation axis of the effector 3 and is in mesh with the transmission spur gear 22. If, accordingly, the transmission spur gear 22 were stationary in this kind of operation, i.e. the pivoting operation, the pivoting movement of the instrument head 4 would cause the output spur gear 21 to roll off the transmission spur gear 22 in the same direction and, thus, would inevitably result in a superimposed rotational movement of the effector 3.

As described in the foregoing, however, the long-face pinion 26 is rotated along with the crank member 8 during a pivoting movement of the handle member I and, thus, drives the drive shaft 24 inside the pushing tube 12. The transmission between the long-face pinion 26 and the drive shaft 24 is calculated such that the transmission gear 22 is rotated by the drive shaft 24 about an angle of rotation corresponding to the angle of rotation which is caused by the output gear 21 during a corresponding bending of the instrument head 4, whereby both rotations compensate each other due to their counter-rotation. In this configuration, the relative position between the transmission spur gear 22 and the output spur gear 21 is maintained even during the bending motion of the instrument head 4, so that the effector 3 is held in each bending position of the instrument head 4 as well as during a bending motion in its current position of rotation with respect to the instrument head 4.

In order to bring about the operation of the effector 3, i.e. the function thereof itself, the lever 7 pivotably supported on the handle member 5 is provided in the present preferred embodiment. As already described in the foregoing concerning FIGS. 6a–6c, lever 7 is operatively connected, via a reversing gear not shown in detail or an appropriate joint mechanism, to the pushing rod 35 which is supported in the rotary shaft 24 and which axially reciprocates relative to the rotary shaft 24 upon a corresponding operation of lever 7. A simple Bowden cable or deflecting lever would also be conceivable for power transmission to the pushing rod 35.

FIG. 6a shows the relative position of the pushing rod 35 and the pushing pin 32 in a bending position of the instrument head 4 of 0° with the tongs being open, FIG. 6b shows the relative position of the pushing rod 35 and the pushing pin 32 in a bending position of the instrument head 4 of approximately 450 with the tongs being open, and FIG. 6c shows the relative position of the pushing rod 35 and the pushing pin 32 in a bending position of the instrument head 4 of approximately 45° with the tongs being closed.

As can be seen from FIGS. 6a–6c, the pushing pin 32 is kept in constant contact with the beveled or chamfered distal front face of the pushing rod 35 by the biasing force of the spring 33. When the pushing rod 35 is shifted in the direction of the instrument head 4 in the case of a 0° bending of the instrument head 4 according to FIG. 6a, the pushing pin 32 is shifted at the same speed and over the same distance as the pushing rod 35, i.e. without transmission, against the biasing force of the spring 33, whereby the jaw 30 of the tongs linked thereto is pivoted in the closing direction.

In this context, it is referred to the fact that, by the shifting action of the pushing rod 35, the pushing pin 32, i.e. especially the center of the pin head radius, remains only approximately on the pivot axis of the instrument head 4, i.e. it moves in a kind of circular orbit during a bending motion of the instrument head 4. As already explained at the beginning of the description of the figures, however, the regulating distances for opening and closing the tongs, for instance, are so small due to the transmissions set that, although the radius of the circular orbit can be calculated theoretically, it has no relevant influence on the position of the tongs for reasons of manufacture already (natural elasticity of the materials used, dimensional tolerances and play at the link joints and gear parts). In other words, the position of the tongs is determined by the position of the lever 7 which, in its turn, is held by an operator and, thus, is also subjected, for instance, to non-controllable movements of the hand (trembling motions). Such disturbances produced due to manual operations are greater by far and, therefore, practically solely relevant compared to those disturbances produced by the afore-described orbit motion.

That is to say, irrespective of the current position of the pushing rod 35 and the pushing pin 32, respectively, a bending of the instrument head 4 does generally not only cause the pushing pin 32 to pivot with respect to the pushing rod 35 but also causes the pin head 34 to slightly slide off the chamfered front face of the pushing rod 35. By this minor slide-off motion, the bearing contact of the pushing pin 32 with the front face is maintained, wherein only such a compensating longitudinal motion of the pushing pin 32 takes place as a result of its slide-off motion, however, which entails no practically relevant change of the closing or opening position at the effector 3. At the same time, however, a kind of power deflection mechanism is provided so as to bring about a longitudinal motion of the pushing rod 35 into a longitudinal motion of the pushing pin 32 now provided at an angular position with respect to the pushing rod 35 by the chamfering of the front face of the pushing bar.

In other words, if the pushing rod 35 is shifted in a bending position >0° according to FIG. 6b in the closing direction of the effector 3, as shown in FIG. 6c, the chamfered front face of the pushing rod 35 slides longitudinally past the pin head 34 while exerting an advance force on the pushing pin 32 which accordingly moves in the closing direction of the effector 3.

It should be understood that any of a variety of fastening means and suitable materials of construction and dimensions may be used to satisfy the particular needs and requirements of the end user. It also will be apparent to those skilled in the art that various modifications and variations can be made in the design and construction of a surgical instrument without departing from the scope or spirit of the invention.

I claim:

1. A surgical instrument comprising an instrument handle linked at a proximal end portion of a tube shaft, the tube shaft having a distal end portion linked to an instrument head supporting an effector rotatable about the longitudinal axis of the tube shaft, the effector being inclinable relative to the tube shaft, wherein the effector further comprises at least one pivotable engaging element operable via an effector operating gear train in cooperation with the instrument handle, wherein the effector operating gear train further comprises a pushing rod shiftably arranged in the tube shaft, and in a linking area between the instrument head and the tube shaft the pushing rod abuts a pushing pin, the pushing pin being shiftably supported in the instrument head and/or the effector and operatively connected to the engaging element.

2. A surgical instrument according to claim 1, wherein the pushing rod has a distal front face that engages the pushing pin and is chamfered at a predetermined angle.

3. A surgical instrument according to claim 2, wherein the predetermined angle is approximately 45°.

4. A surgical instrument according to claim 2, wherein the pushing pin has a ball-shaped pin head engaging the distal front face of the pushing rod.

5. A surgical instrument according to claim 2, wherein a biasing element forces the pushing pin against the distal front face of the pushing rod.

6. A surgical instrument according to claim 5, wherein the biasing element is a spring.

7. A surgical instrument according to claim 3, wherein a biasing element forces the pushing pin against the distal front face of the pushing rod.

8. A surgical instrument according to claim 7, wherein the biasing element is a spring.

9. A surgical instrument according to claim 2, wherein the pushing rod and the pushing pin are aligned coaxially to each other when the instrument head is inclined at 0° with respect to the tube shaft.

10. A surgical instrument according to claim 4, wherein a center of the pin head is located approximately in a pivot axis of the instrument head when the instrument head is inclined at 0° with respect to the tube shaft.

11. A surgical instrument according to claim 2 wherein chamfering at an end of a pushing rod side is aligned approximately perpendicularly to a direction of inclination of the instrument head.

\* \* \* \* \*